(12) United States Patent
Lindner et al.

(10) Patent No.: US 10,413,343 B2
(45) Date of Patent: Sep. 17, 2019

(54) OUT-OF-ROUND PEDICLE SCREW

(71) Applicant: Aesculap AG, Tuttlingen (DE)

(72) Inventors: Stephan Lindner, Wurmlingen (DE); Juan-Jose Bogajo, Wurmlingen (DE)

(73) Assignee: Aesculap AG (DE)

( * ) Notice: Subject to any disclaimer, the term of this patent is extended or adjusted under 35 U.S.C. 154(b) by 707 days.

(21) Appl. No.: 14/900,263

(22) PCT Filed: Jun. 25, 2014

(86) PCT No.: PCT/EP2014/063401
§ 371 (c)(1),
(2) Date: Dec. 21, 2015

(87) PCT Pub. No.: WO2014/207044
PCT Pub. Date: Dec. 31, 2014

(65) Prior Publication Data
US 2016/0367304 A1 Dec. 22, 2016

(30) Foreign Application Priority Data

Jun. 27, 2013 (DE) .................. 10 2013 106 758

(51) Int. Cl.
*A61B 17/86* (2006.01)
*A61B 17/70* (2006.01)

(52) U.S. Cl.
CPC ...... *A61B 17/8625* (2013.01); *A61B 17/7035* (2013.01)

(58) Field of Classification Search
CPC ............ F16B 25/0078; F16B 25/00582; F16B 25/0057; A61B 17/863; A61B 17/8625
See application file for complete search history.

(56) References Cited

U.S. PATENT DOCUMENTS

| | | | | |
|---|---|---|---|---|
| 2,165,011 A | * | 7/1939 | Rosenberg | B21H 3/027 411/420 |
| 2,532,296 A | * | 12/1950 | Giesen | A61B 17/863 408/1 R |
| 3,246,556 A | * | 4/1966 | Phipard, Jr. | B21H 3/027 411/416 |

(Continued)

FOREIGN PATENT DOCUMENTS

| | | |
|---|---|---|
| CN | 1527908 A | 9/2004 |
| CN | 101360922 A | 2/2009 |

(Continued)

OTHER PUBLICATIONS

Notification of Reasons for Rejection for Japanese Application No. 2016-522468, dated Feb. 27, 2018 with translation, 9 pages.

(Continued)

*Primary Examiner* — David W Bates
(74) *Attorney, Agent, or Firm* — RatnerPrestia

(57) ABSTRACT

A medical bone screw in particular in pedicle screw design includes a screw-and-thread shaft which has a distal shaft portion of a preferably smaller core diameter that transitions into a proximal shaft portion of a preferably larger core diameter, whose proximal end is provided with a screw head. The core cross-sectional shape along the distal shaft portion is formed to be out-of-round, preferably polygonal, and the core cross-sectional shape along the proximal shaft portion is formed to be circular.

12 Claims, 6 Drawing Sheets

(56) References Cited

U.S. PATENT DOCUMENTS

Figure 1:
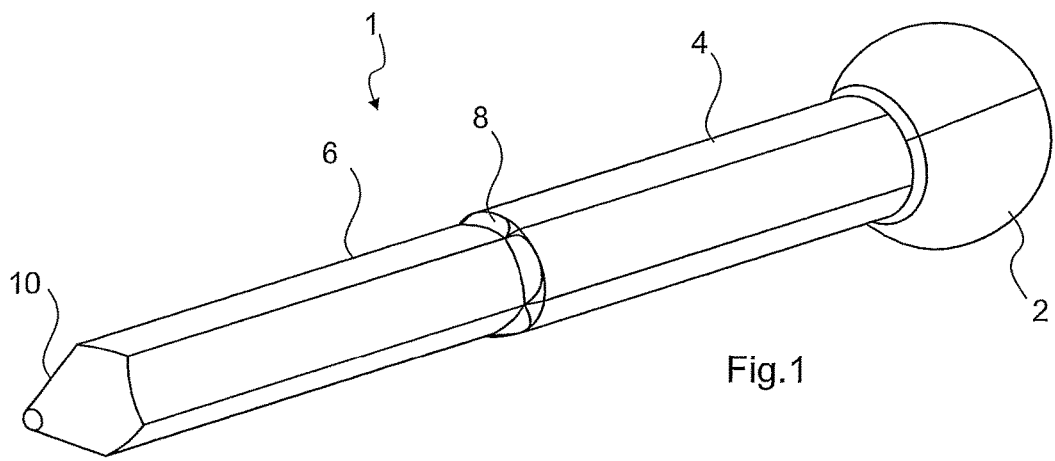

| | | | | |
|---|---|---|---|---|
| 3,258,797 | A * | 7/1966 | Budd | B21H 3/10 408/26 |
| 3,370,501 | A * | 2/1968 | Ansingh | F16B 5/0275 411/387.2 |
| 3,454,070 | A | 7/1969 | Phipard | |
| 3,472,119 | A * | 10/1969 | Peterson, Jr. | F16B 25/0021 411/422 |
| 4,046,051 | A * | 9/1977 | Lovisek | B21H 3/027 411/386 |
| 4,235,149 | A * | 11/1980 | Veldman | B21H 3/027 411/417 |
| 5,044,853 | A * | 9/1991 | Dicke | F16B 25/0052 411/311 |
| 5,385,439 | A * | 1/1995 | Hurdle | F16B 25/0052 411/311 |
| 5,601,553 | A | 2/1997 | Trebing et al. | |
| 5,733,307 | A * | 3/1998 | Dinsdale | A61B 17/0401 606/104 |
| 5,897,280 | A * | 4/1999 | Dicke | F16B 25/0015 411/386 |
| 6,056,491 | A * | 5/2000 | Hsu | F16B 25/0015 411/311 |
| 6,254,327 | B1 * | 7/2001 | Chen | F16B 25/0015 411/310 |
| 6,347,917 | B1 * | 2/2002 | Kato | B21K 1/56 411/308 |
| 6,468,014 | B2 * | 10/2002 | Chen | F16B 25/0015 411/387.4 |
| 6,494,656 | B1 | 12/2002 | Boyer | |
| 7,101,133 | B2 * | 9/2006 | Dicke | F16B 25/0015 411/308 |
| 7,156,600 | B2 * | 1/2007 | Panasik | B21H 3/02 411/308 |
| 7,677,854 | B2 | 3/2010 | Langewiesche | |
| 8,128,671 | B2 | 3/2012 | Taylor | |
| 8,360,702 | B2 * | 1/2013 | Yu | F16B 25/0015 411/386 |
| 8,403,972 | B2 | 3/2013 | Hasenbohler | |
| 8,926,249 | B2 * | 1/2015 | Lin | F16B 25/0057 411/386 |
| 9,523,383 | B2 * | 12/2016 | Park | F16B 25/0057 |
| 9,848,927 | B2 * | 12/2017 | Giorno | A61B 17/863 |
| 2002/0127084 | A1 * | 9/2002 | Hsu | F16B 25/0015 411/387.4 |
| 2002/0141848 | A1 * | 10/2002 | Hsu | F16B 12/14 411/411 |
| 2003/0049095 | A1 | 3/2003 | Boyer et al. | |
| 2005/0038438 | A1 | 2/2005 | Anderson et al. | |
| 2007/0156154 | A1 * | 7/2007 | Schlienger | A61B 17/863 606/309 |
| 2007/0160440 | A1 | 7/2007 | Langewiesche | |
| 2007/0282341 | A1 * | 12/2007 | Hes | A61B 17/863 606/328 |
| 2008/0177335 | A1 * | 7/2008 | Melkent | A61B 17/7001 606/309 |
| 2008/0249579 | A1 * | 10/2008 | Taylor | A61B 17/863 606/317 |
| 2008/0292429 | A1 | 11/2008 | Hasenbohler | |
| 2011/0152948 | A1 | 6/2011 | Crook | |
| 2012/0172935 | A1 * | 7/2012 | Willert | A61B 17/8625 606/309 |
| 2013/0253594 | A1 | 9/2013 | Zucherman | |
| 2014/0142636 | A1 * | 5/2014 | Hes | A61B 17/863 606/279 |
| 2014/0277193 | A1 * | 9/2014 | Mobasser | A61B 17/8625 606/311 |
| 2014/0314523 | A1 * | 10/2014 | Lin | F16B 25/0057 411/387.4 |
| 2017/0196611 | A1 * | 7/2017 | Shmueli | A61B 17/8625 |

FOREIGN PATENT DOCUMENTS

| | | |
|---|---|---|
| CN | 201925301 U | 8/2011 |
| DE | 202006000479 | 4/2006 |
| DE | 60211920 | 10/2006 |
| EP | 1207312 | 5/2002 |
| JP | S5260557 U | 5/1977 |
| JP | 5842409 | 3/1983 |
| JP | H08206143 A | 8/1996 |
| JP | H1043199 A | 2/1998 |
| JP | 2009513899 A | 4/2009 |
| RU | 111756 U1 | 12/2011 |
| RU | 2452424 C1 | 6/2012 |
| RU | 2475205 C2 | 2/2013 |
| WO | 2007048267 | 5/2007 |
| WO | 2007048267 A1 | 5/2007 |

OTHER PUBLICATIONS

Decision of Grant for Russian Application No. 2016102174, dated Nov. 21, 2017 with translation, 9 pages.

Chinese Office Action for Chinese Application No. 201480035702.1, dated Jul. 26, 2017, including English translation, 12 pages.

German Search Report for German Application No. 10 2013 106 758.1 dated Jan. 21, 2014, including partial translation.

International Search Report for International Application No. PCT/EP2014/063401 dated Sep. 2, 2014.

Notification of Reasons for Rejection for Japanese Application No. 2016-522468, dated Aug. 29, 2017, including English translation, 11 pages.

Canadian Examination Report for Canadian Application No. 2909350, dated Mar. 19, 2018, 3 pages.

\* cited by examiner

OUT-OF-ROUND PEDICLE SCREW

RELATED APPLICATIONS

This is the U.S. National Phase entry of International Application No. PCT/EP2014/063401, filed Jun. 25, 2014, which is related to and claims the benefit of priority of German Application No. 10 2013 106 758.1, filed Jun. 27, 2013. The contents of International Application No. PCT/EP2014/063401 and German Application No. 10 2013 106 758.1 are incorporated by reference herein in their entireties and for all purposes.

FIELD

The present invention relates to a pedicle screw comprising a screw core profile with a cross-section which is out-of-round at least in parts.

BACKGROUND

A pedicle screw is a surgical instrument/implant for stabilizing the vertebral column. In backbone surgery, pedicle screws are frequently used for stabilizing operations such as for repositioning a sliding vertebra or for stiffening vertebrae. Their usually self-tapping thread facilitates the process of screwing the screw in the vertebral arch roots of two or more vertebrae. The screw head or the tulip is either supported on the screw shaft in movable fashion (polyaxial) by means of a ball joint or rigidly connected (mono-axial) to the thread.

Provided in the screw head/tulip is an axially extending, U-shaped recess capable of receiving a rod. Said rod is fixed in the screw head/tulip by means of a set screw. Hence, the pedicle screw may be used as an instrument to return a displaced vertebra (sliding vertebra) back to the correct position, for example. For stabilizing the vertebral column, four or more pedicle screws are interconnected by means of rods along the backbone axis. Pedicle screws having the previously described construction are known in the prior art from many disclosures to which reference is made in the following description. This is why a repeated description of the pedicle screw, in particular of the tulip and the traverse, may be omitted with reference to said commonly known prior art.

Regarding the screw shaft, however, pedicle screw shapes are known from prior art which have different core cross-sections (expanding continuously or in step-wise manner) in the longitudinal direction of the shaft. This measure is supposed to ensure that a pedicle screw which is screwed in the vertebral arch root gets radially braced in particular in the outer/proximal head zone in the borehole and thus is able to transmit higher forces into the vertebra without coming loose. It was also contemplated to radially expand the screw flanks in the longitudinal direction of the shaft toward the screw head in a continuous or step-wise manner in order to achieve an increasing incising effect in the vertebral body. This is done with the aim to prevent the pedicle screw from breaking out.

Despite of these commonly known efforts in terms of providing an optimum design of the shaft and the screw flanks, the urgent problem of the reliable grip of the pedicle screw in the vertebra over a long period of time continues to exist. In particular, following defects in the prior art turn out to be particularly fatal:

An insufficient secondary stability with respect to rotational forces acting on the pedicle screw,
if the pedicle screw is torn out of the bone in case of tensile and/or shearing forces,
stiff and slow screwing process,
uncontrollability of the screwing process.

In fact, there is a variety of different screw shapes and screw constructions in the field of screw technology, but these are designed outside the field of medical engineering with regard to specific applications such as cooperating with wood, plastics, plasterboards and the like construction materials. Bone material is clearly different from these, not only due to its composition and strength but also because of the fact that it is a material which is still alive and constantly changes and renews its structure. In addition, conventional screws outside the field of medical engineering are exposed to other loads (mostly static loads) than in a medical application in the body of a patient. This is why they can be made from other materials which result in an optimum connection with the construction material concerned. In medical technology, this is not possible (or only partly possible) due to reasons of hygiene as well as biocompatibility. This is why technical solutions outside the field of medical engineering can not be readily transferred to bone screw constructions.

SUMMARY

On the basis of these problems, it is the object of the present invention to provide a bone screw, in particular a pedicle screw, by means of which higher forces can be reliably and permanently introduced into a patient's bone. In particular, the bone screw or pedicle screw is to be optimized preferably to the extent that a higher secondary stability in terms of rotational forces is achieved.

This object as well as further aims of the present invention are achieved by a bone screw comprising the features described herein.

The fundamental principle of the present invention is based on the consideration to subdivide the threaded shaft of a bone screw or pedicle screw into at least two longitudinal sections, i.e. a distal shaft portion and a (preferably directly) adjoining proximal shaft portion. It is exclusively the distal shaft portion which has—with regard to its thread core—a cross-sectional shape extending in the longitudinal direction of the distal shaft portion which deviates from a circular shape. Owing to this "out-of-round" cross-sectional shape of the thread core which is exclusively present in the distal shaft portion, the bone/pedicle screw is able to receive a defined surplus of rotational forces than in the case of a thread core with a continuous circular shape, without coming loose in the bone or further getting screwed into it. As the circular shape of the thread core is maintained in the proximal shaft portion, however, the bone/pedicle screw may continue to be firmly braced in the patient's bone in particular in the area adjoining the bone and in this way permanently transmit shearing forces into the bone. In this context, reference is made to the fact that the distal shaft portion has a defined section length (approximately 0.5 times the total shaft length) with a (constant) small (median) core diameter. The proximal shaft portion also has a defined section length (approximately 0.5 times the total shaft length) with a (constant) large (median) core diameter.

Preferably, provision is made that the out-of-round core cross-sectional shape represents a polygon further comprising preferably sharp-edged corners. This enhances the ability of receiving/transmitting rotational forces into the bone.

According to an aspect of the invention possibly to be claimed independently, provision may be made that the number of the corners changes over the longitudinal extension of the distal shaft portion. In this way, a square shape may be formed in the distal zone first, changing over into in a pentagonal or hexagonal shape in the middle area of the distal shaft portion. This will further enhance the load-bearing capacity in terms of rotational forces.

According to an aspect of the invention possibly to be claimed independently, provision may be made that the corners between respectively longitudinally adjacent screw threads are arranged one behind the other at the same angular position along the distal shaft portion. As an alternative to this, however, it is also possible that the corners between respectively longitudinally adjacent screw threads are arranged so as to be angularly staggered with respect to each other. In the latter case, provision can be made that the angular displacement amount and/or the angular displacement direction changes continuously and/or abruptly in the longitudinal direction of the shaft. These irregularities allow to introduce larger rotational forces into the bone and there will be a safe grip of the bone screw in the bone material.

According to an aspect of the invention possibly to be claimed independently, the screw shaft and preferably the distal shaft portion having the out-of-round core diameter may be manufactured by a thread whirling process by means of a thread whirling tool. This measure results in substantially sharp-edged corners on the core perimeter, improving the ability to transfer rotational forces into the bone.

It may be advantageous if the outer edges of the screw flanks have the shape of a continuous spiral even in the zone of the distal shaft portion. In particular, it may be advantageous if the outer edges of the screw flanks are formed without any bends and edges especially in the distal shaft portion. This guarantees a reliable screw connection to the bone and high tensile forces can be introduced into the bone via the screw flanks without the screw being torn out.

BRIEF DESCRIPTION OF THE DRAWING FIGURES

The invention will be explained in more detail below on the basis of preferred exemplary embodiments with reference to the accompanying Figures.

Figure 2:
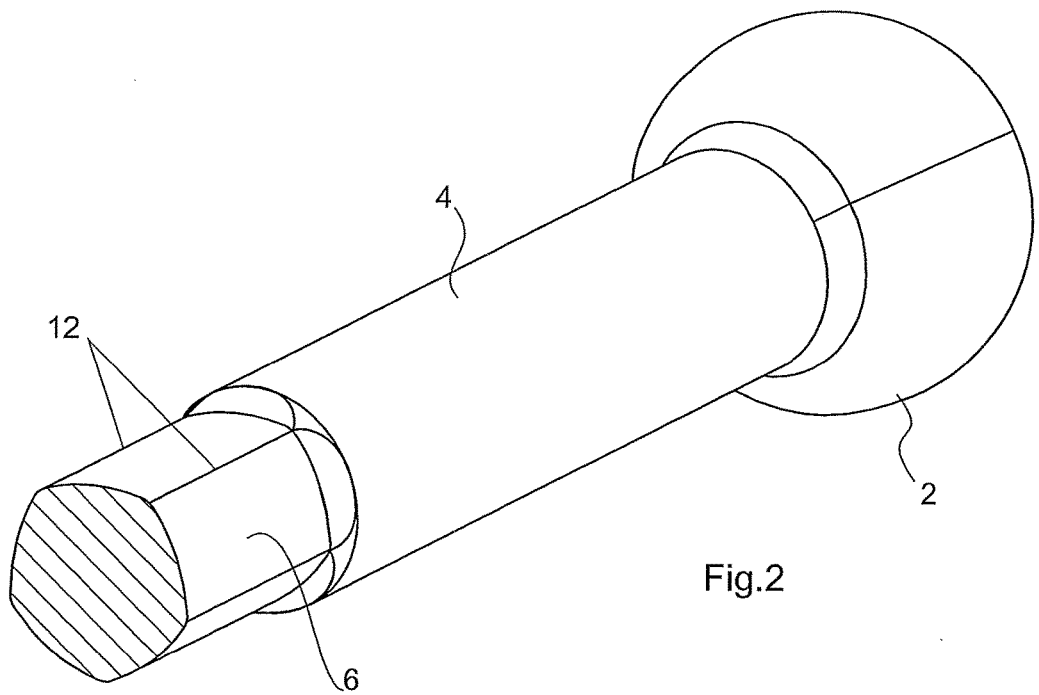
Figure 3:
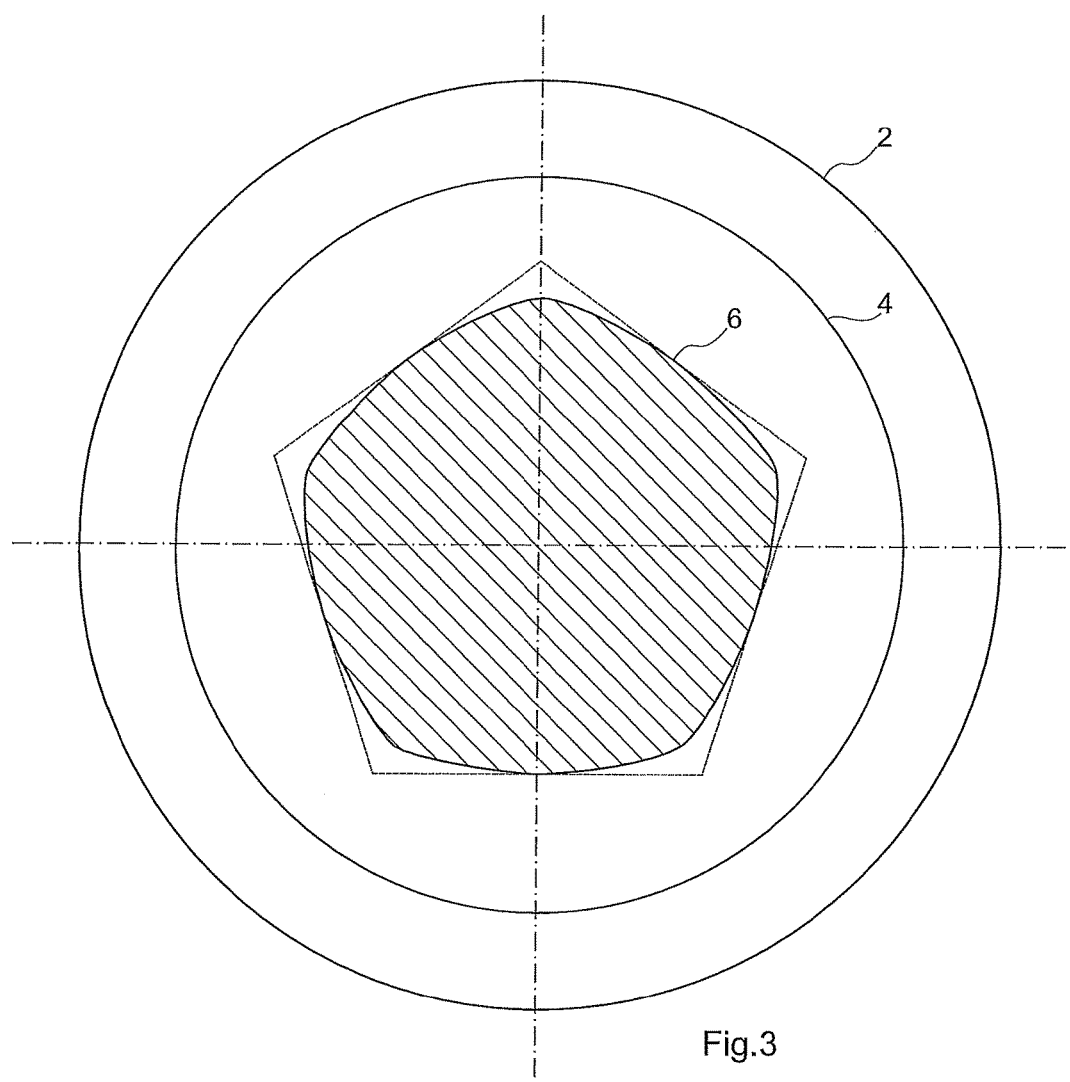
Figure 4:
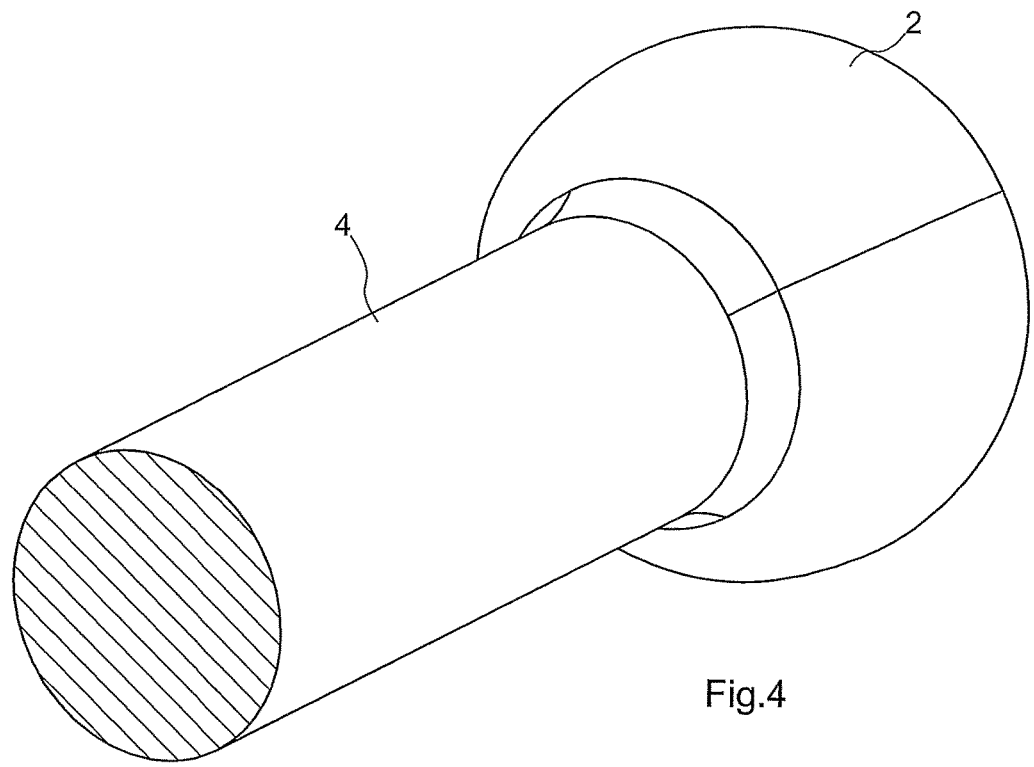
Figure 5:
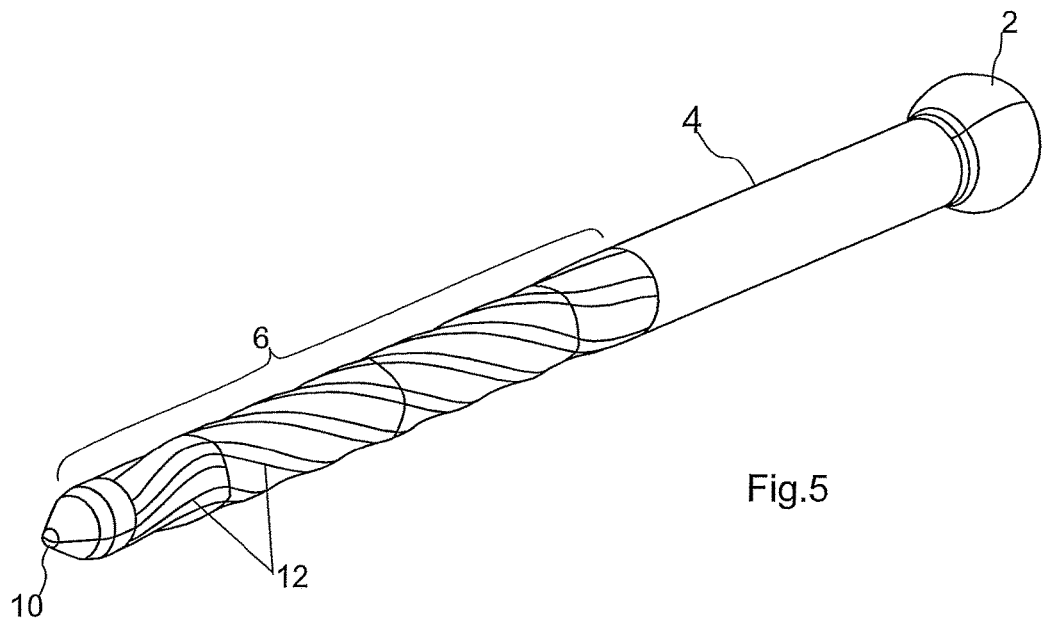
Figure 6:
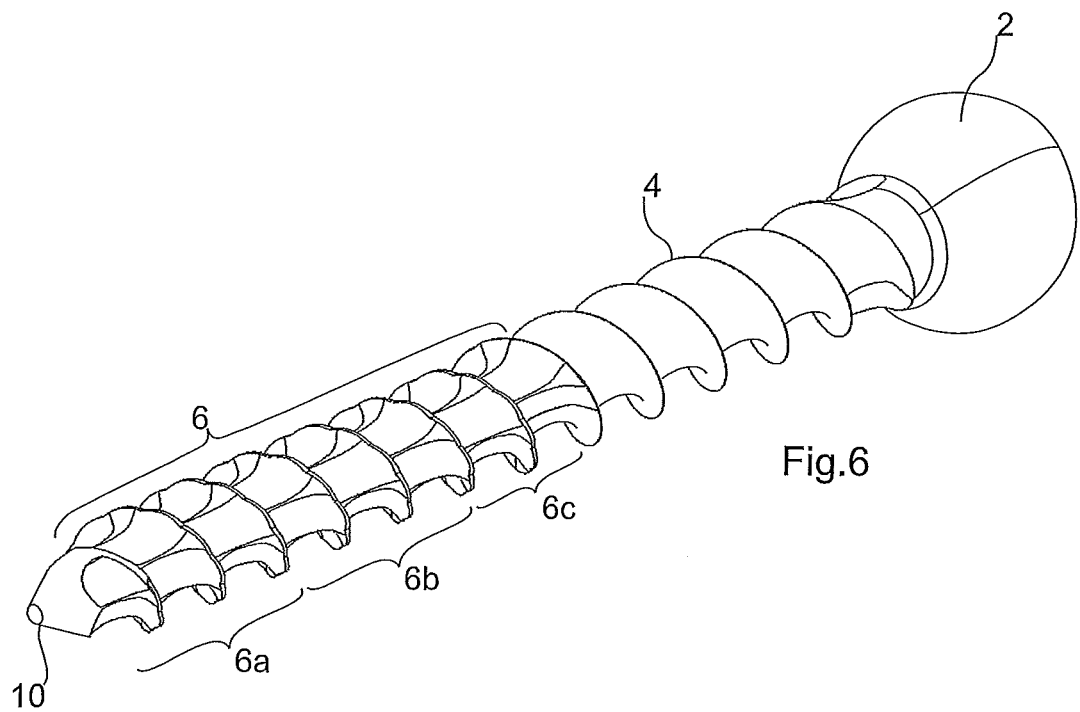
Figure 7:
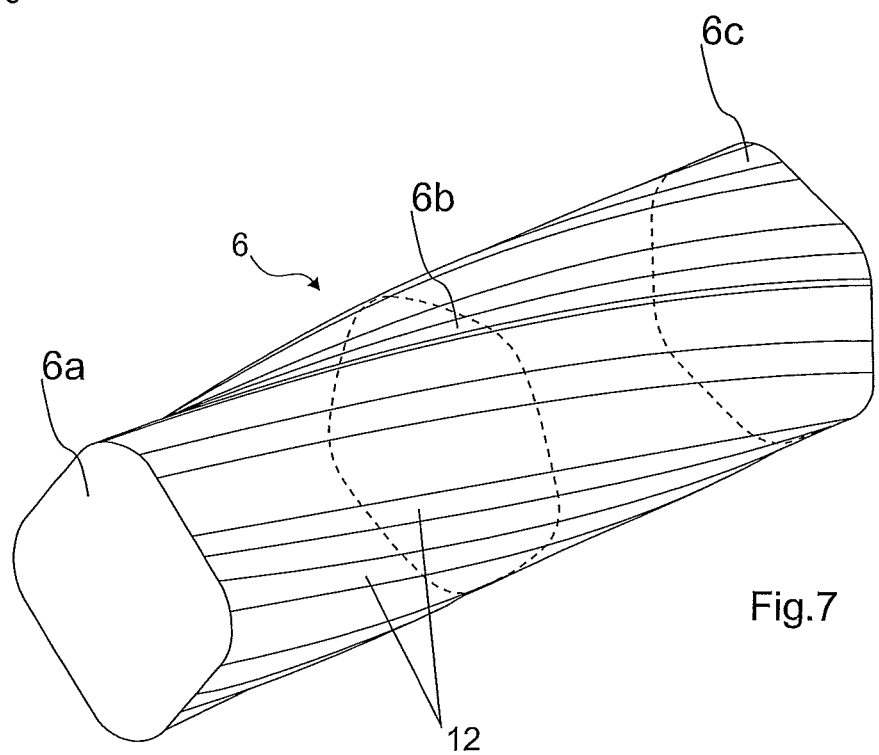
Figure 8:
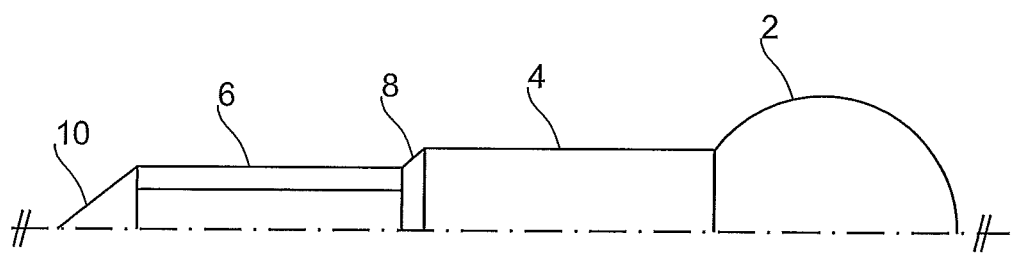
Figure 9:
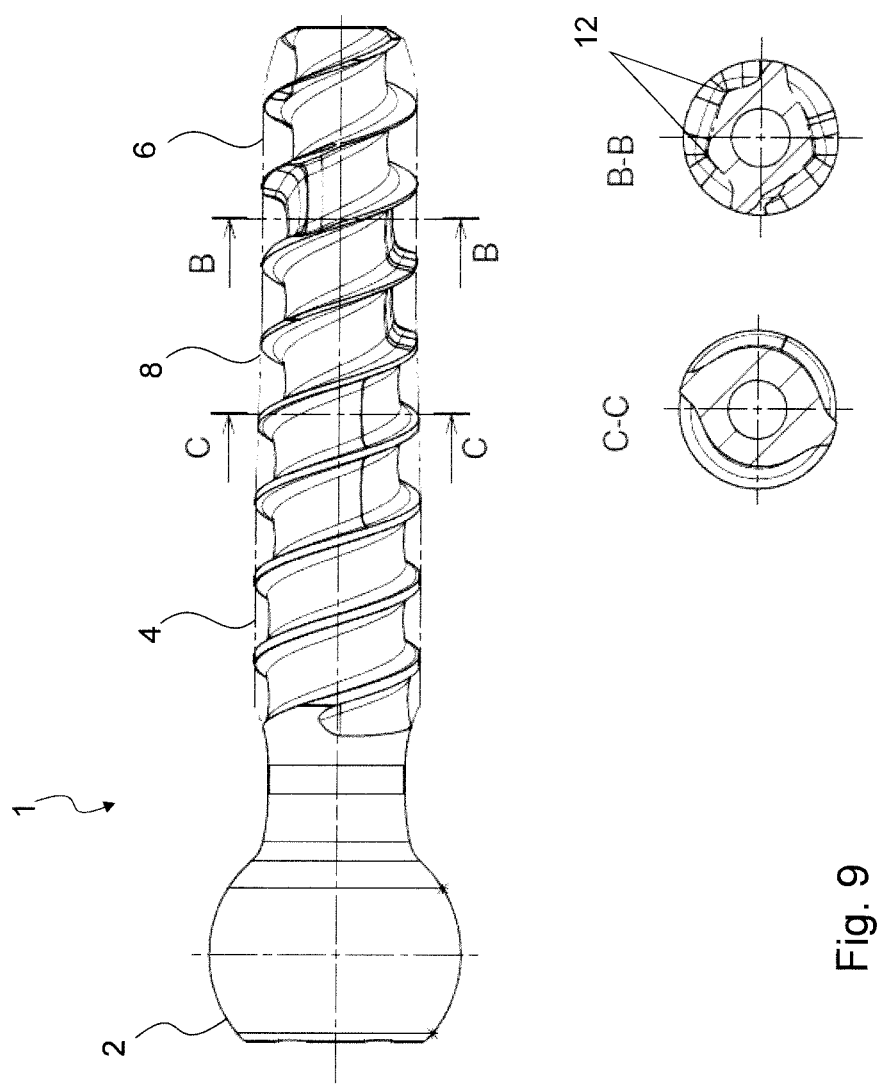

FIG. 1 shows a perspective view of the thread core of a bone screw, in particular a pedicle screw, according to a first preferred exemplary embodiment of the invention without thread flank and tulip, FIG. 2 shows a cross-sectional view of the thread core in the distal shaft portion of the bone screw according to FIG. 1 without thread flank and tulip, FIG. 3 shows the cross-section of the thread core in the distal shaft portion of the bone screw according to FIG. 1, FIG. 4 shows a cross-sectional view of the thread core in the proximal shaft portion of the bone screw according to FIG. 1 without thread flank and tulip, FIG. 5 shows the perspective view of the thread core of a bone screw, in particular a pedicle screw, according to a second preferred exemplary embodiment of the invention without thread flank and tulip, FIG. 6 shows the perspective view of the thread core of a bone screw, in particular a pedicle screw, according to a third preferred exemplary embodiment of the invention without thread flank and tulip, FIG. 7 shows in a perspective view the schematic longitudinal extension of the longitudinal edges which are produced by the polygonal core cross-sectional shape in the distal shaft portion, FIG. 8 shows the basic extension of the thread core of a bone screw according to a preferred exemplary embodiment of the invention, and FIG. 9 shows an elevation view and relevant cross sections showing the threadform of a bone screw according to FIG. 1.

DETAILED DESCRIPTION

The bone screw illustrated in FIGS. 1 to 3 and 9 preferably in the form of a pedicle screw according to a first preferred exemplary embodiment of the invention comprises a screw shaft 1 and a ball-head shaped screw head 2 on the proximal end of the screw shaft 1. The screw head 2 is adapted to be pivotally coupled to a cylindrical tulip which is not shown in further detail, said tulip being provided with an elongated slot which is open axially at one side starting from the proximal tulip end and is provided for transversely inserting a traverse or bar (likewise not shown in further detail). Such a tulip construction according to a polyaxial pedicle screw is well known from the prior art, so that reference can be made here to the pertinent prior art.

According to the invention, the screw shaft 1 is subdivided in several, preferably two longitudinal sections 4, 6. In the present case, a proximal longitudinal section 4 immediately adjoining the screw head 2 in longitudinal direction has a larger (median) core diameter which is cylindrical according to this exemplary embodiment, i.e. has a continuously circular cross-section in longitudinal direction. Basically, the proximal longitudinal section 4 may have a core diameter which is constant over its axial length. It is also conceivable, however, that the core diameter decreases continuously or in step-wise manner from the screw head 2 toward the distal end.

The screw flanks which are not shown in FIGS. 1 to 3 usually have a sharp-edged outer edge without any bends, the outer diameters of screw flanks preferably following the core diameter. This means that in case of a varying core diameter, the outer diameters of the screw flanks will vary in corresponding fashion. This ensures that the screw thread will always cut into the bone to a sufficient extent and in this way is able to introduce maximum tensile forces into the bone.

The proximal shaft portion 4 shown in FIGS. 1 and 2 having a cylindrical core cross-section transitions into a distal shaft portion 6 in a middle area 8 of the screw shaft 1; this distal shaft portion has a (median) core diameter which is smaller than the core diameter of the proximal shaft portion 4. Here, it is referred to the fact that both shaft portions 4, 6 may alternatively have substantially the same core diameter, too. Further, the core diameter of the distal shaft portion 6 is shown in the present exemplary embodiment so as to be constant over the entire section length. It is also conceivable, however, that the core diameter of the distal shaft portion 6 is further decreased continuously or in step-wise manner toward the screw tip 10.

The important point in the present invention is that (exclusively) the distal shaft portion 6 is realized with a core cross-section that deviates from the cylindrical shape (circular shape). In other words, the (small, median) core cross-section of the distal shaft portion 6 has a polygonal shape over its entire length, preferably with equal legs. In particular, the (small, median) core cross-section according to FIG. 3 has five corners in total, with this polygonal shape adjoining the circular shape of the proximal shaft portion 4 according to FIG. 4 essentially without any transition. Further, the outer diameter of the screw may be circular, especially also in the zone of the polygon portion irrespectively of the polygonal shape of the screw core (substantially without any bends), as is indicated in FIG. 6.

According to the first preferred exemplary embodiment, the five corners of the polygonal shape are always formed at the same angular position over the entire length of the distal shaft portion. This arrangement results according to FIG. 2 in five axially parallel, straight outer lines/edges 12. As an alternative according to a second exemplary embodiment of the present invention, it is however also possible to vary the angular positions of the corners along the distal shaft portion 6, as is schematically shown in particular in FIG. 5.

Accordingly, the corners of a polygonal core cross-sectional shape, starting from the screw tip 10 and proceeding in proximal direction, are initially continuously twisted in anti-clockwise direction and subsequently are continuously twisted in reverse fashion in clockwise direction. This results in S-shaped or zigzag-shaped, longitudinally extending outer lines/edges 12 on the screw core.

As an alternative or in addition to the previously described measures, the distal shaft portion 6 may be subdivided in several axial zones in which the (small, median) core cross-sections each have a polygonal shape with different numbers of corners with respect to one another, as is illustrated in FIG. 6. Accordingly, the distal shaft portion 6 may be subdivided, for example, in three axial zones 6a, 6b, 6c, the number of the corners of the respective polygonal shape starting from the screw tip 10 changing from four to five and then to six. Basically, zones comprising from two to any number of corners are conceivable. This results in a screw contour of the screw core as it is indicated in FIG. 7.

In order to be able to produce the polygonal cross-sectional shape of the screw core in precise manner, a thread whirling tool of known construction is employed according to the invention. According to this, the "out-of-round" and preferably polygonal core cross-section is manufactured in that the thread whirling tool within a rotation of the bone screw by 360° is repeatedly oscillated or moved around its own axis toward the thread core. The oscillating movement generated in this process preferably amounts to between +/−0.05 mm and +/−1 mm. By way of example and in a preferred embodiment of the invention, the thread whirling tool (or alternatively the thread core) may oscillate between a feed length of 3.2 mm and 3.7 mm. Between these two feed lengths, the corners are produced which are essentially sharp-edged depending on how fast the feed lengths are changed compared to the number of revolutions.

In the cylindrical, proximal shaft portion 4, the thread core will be machined to a thread core diameter of e.g. 4 mm within two full revolutions of the bone screw around its axis. This produces the uniform transition 8 from the distal shaft portion 6 to the proximal shaft portion 4.

Finally, FIG. 8 shows the cross-sectional profile of the screw core according to a preferred exemplary embodiment of the invention in principle. Accordingly, the bone screw according to the invention comprises the screw tip 10 which transitions in conical fashion into the distal shaft portion 6 which in the present case has a constant, small core diameter. Only this portion 6 having the constantly small core diameter is provided for the formation of the polygonal cross-sectional shape of the screw core. In a middle area of the screw shaft, the transition portion 8 is formed which has a conically expanding core cross-section, continuing into the proximal shaft portion 4 with a constantly large core diameter (cylindrical shape). This proximal shaft portion 4 has a core cross-section of circular shape.

In summary, the disclosure relates to a medical bone screw in particular in pedicle screw design comprising a screw-and-thread shaft 1 which comprises a distal shaft portion 6 having a preferably smaller, but not necessarily a preferably constant (median) core diameter that transitions into a proximal shaft portion 4 having a preferably larger, but not necessarily a preferably constant (median) core diameter whose proximal end is provided with a screw head 2. According to the invention, the core cross-sectional shape along the distal shaft portion 6 is formed to be out-of-round at least in parts, preferably polygonal, and the core cross-sectional shape along the proximal shaft portion 4 is formed to be circular.

The invention claimed is:

1. A medical bone screw comprising a screw head and a threaded shaft, the threaded shaft having a proximal most end, a distal most end, and a transition between the proximal most end and the distal most end, the threaded shaft comprising:
   a threaded distal shaft portion having a first core and a first axial length, the first axial length beginning adjacent the transition and ending at the distal most end, the first core having a first diameter which is constant along the first axial length of the threaded distal shaft portion; and
   a threaded proximal shaft portion having a second core and a second axial length, the second axial length beginning adjacent the proximal most end and ending at the transition, the second core having a second diameter which is constant along the second axial length of the threaded proximal shaft portion, the second diameter of the second core being greater than the first diameter of the first core,
   the first core being formed to be out-of-round along the first axial length and the second core formed to be circular along the second axial length,
   wherein the first core has a first cross-sectional shape, the first cross-sectional shape being a polygon with a number of corners and equal legs, and
   the outer diameter of the screw along the first axial length is circular irrespectively of the first cross-sectional shape of the first core.

2. The medical bone screw according to claim 1, wherein the number of corners changes along the first axial length of the threaded distal shaft portion.

3. The medical bone screw according to claim 1, wherein the threaded distal shaft portion comprises a plurality of threads, and wherein the corners on the first core between respectively longitudinally adjacent screw threads are arranged one behind the other at the same angular position along the threaded distal shaft portion.

4. The medical bone screw according to claim 1, wherein the threaded distal shaft portion comprises a plurality of threads, and wherein the corners on the first core between respectively longitudinally adjacent screw threads are arranged so as to be angularly staggered by an angular displacement with respect to each other.

5. The medical bone screw according to claim 4, wherein a direction and/or an amount of the angular displacement changes continuously and/or abruptly along the first axial length of the threaded distal shaft portion.

6. The medical bone screw according to claim 1, wherein the threaded shaft is manufactured by a thread whirling process utilizing a thread whirling tool at least in a zone of the threaded distal shaft portion.

7. The medical bone screw according to claim 1, wherein the threaded proximal shaft section and the threaded distal shaft section comprise a plurality of screw flanks, the screw flanks comprising outer edges each having a diameter, the outer edges of the screw flanks, even along the threaded distal shaft portion, form a continuous spiral, the diameters of the outer edges following the core diameter.

8. The medical bone screw according to claim 7, wherein the screw flanks in the distal shaft portion are shaped so as to have no kinks or sharp edges.

9. The medical bone screw according to claim 1, wherein a sleeve-shaped tulip for receiving a longitudinal rail is pivotally coupled to the screw head.

10. A medical bone screw comprising a screw head and a threaded shaft, the threaded shaft having a proximal most end, a distal most end, and a transition between the proximal most end and the distal most end, the threaded shaft comprising:
- a threaded distal shaft portion having a first core and a first axial length, the first axial length beginning adjacent the transition and ending at the distal most end, the first core having a first diameter which is constant along the first axial length of the threaded distal shaft portion; and
- a threaded proximal shaft portion having a second core and a second axial length, the second axial length beginning adjacent the proximal most end and ending at the transition, the second core having a second diameter which is constant along the second axial length of the threaded proximal shaft portion, the second diameter of the second core being greater than the first diameter of the first core,
- the first core being formed to be out-of-round along the first axial length and the second core formed to be circular along the second axial length,
- wherein the first core has a first cross-sectional shape, the first cross-sectional shape being a polygon with a number of corners, and
- wherein the number of corners changes along the first axial length of the threaded distal shaft portion.

11. A medical bone screw comprising a screw head and a threaded shaft, the threaded shaft having a proximal most end, a distal most end, and a transition between the proximal most end and the distal most end, the threaded shaft comprising:
- a threaded distal shaft portion having a first core and a first axial length, the first axial length beginning adjacent the transition and ending at the distal most end, the first core having a first diameter which is constant along the first axial length of the threaded distal shaft portion; and
- a threaded proximal shaft portion having a second core and a second axial length, the second axial length beginning adjacent the proximal most end and ending at the transition, the second core having a second diameter which is constant along the second axial length of the threaded proximal shaft portion, the second diameter of the second core being greater than the first diameter of the first core,
- the first core being formed to be out-of-round along the first axial length and the second core formed to be circular along the second axial length,
- wherein the first core has a first cross-sectional shape, the first cross-sectional shape being a polygon with a number of corners, and
- wherein the threaded distal shaft portion comprises a plurality of threads, and wherein the corners on the first core between respectively longitudinally adjacent screw threads are arranged so as to be angularly staggered by an angular displacement with respect to each other.

12. The medical bone screw according to claim 11, wherein a direction and/or an amount of the angular displacement changes continuously and/or abruptly along the first axial length of the threaded distal shaft portion.

* * * * *